United States Patent [19]

Nakanishi et al.

[11] Patent Number: 5,034,188
[45] Date of Patent: Jul. 23, 1991

[54] ARTIFICIAL LUNG

[75] Inventors: Hikaru Nakanishi, Kawasaki; Katsuyuki Kuwana; Shuichi Ishii, both of Yokohama, all of Japan

[73] Assignee: Senko Medical Instrument Mfg. Co., Ltd., Tokyo, Japan

[21] Appl. No.: 154,638

[22] Filed: Feb. 9, 1988

[30] Foreign Application Priority Data

Feb. 9, 1987 [JP] Japan .................................. 62-17494

[51] Int. Cl.⁵ ............................................. A61M 1/14
[52] U.S. Cl. ......................................... 422/46; 422/48; 128/DIG. 3; 261/DIG. 28; 55/16; 55/158; 210/321.74; 210/321.83
[58] Field of Search ............. 422/46, 48; 128/DIG. 3; 261/DIG. 28; 55/16, 158; 210/321.74, 321.83

[56] References Cited

U.S. PATENT DOCUMENTS

| | | | |
|---|---|---|---|
| 3,422,008 | 1/1969 | McLain | 210/321.83 |
| 4,188,360 | 2/1980 | Kurata | 422/46 |
| 4,205,042 | 5/1980 | Lobdell et al. | 128/DIG. 3 |
| 4,336,224 | 6/1982 | Siposs | 422/46 |
| 4,374,088 | 2/1983 | Stenberg et al. | 261/DIG. 28 |
| 4,424,190 | 1/1984 | Mather, III et al. | 55/158 |
| 4,440,723 | 4/1984 | Gordon | 422/46 |
| 4,451,562 | 5/1984 | Elgas et al. | 422/48 |
| 4,533,516 | 8/1985 | Johnsson et al. | 422/46 |
| 4,620,965 | 11/1986 | Fukusawa et al. | 422/46 |
| 4,639,353 | 1/1987 | Takemura et al. | 422/46 |
| 4,645,645 | 2/1987 | Martinez et al. | 422/48 |
| 4,656,004 | 4/1987 | Stewart | 422/46 |
| 4,698,207 | 10/1987 | Bringham et al. | 422/46 |
| 4,874,581 | 10/1989 | Sutherland et al. | 422/46 |

Primary Examiner—Robert J. Warden
Assistant Examiner—Lynn M. Kummert
Attorney, Agent, or Firm—Darby & Darby

[57] ABSTRACT

An artificial lung comprises a venous blood reservoir to receive and store venous blood. A heat exchanger communicating with the venous blood reservoir receives the venous blood so the blood temperature is regulated by heat exchange through a wall between flowing water and the venous blood. A blood oxygenator concentrically disposed within a hollow space of said heat exchanger comprises a cylindrical body defining a cylindrical space and at least one gas permeable membrane separating said cylindrical space into a first space and a second space. The first space receives the venous blood from the heat exchanger and the second space communicates with an oxygenating gas feed line so that the blood is oxygenated through the gas permeable membrane.

9 Claims, 5 Drawing Sheets

ARTIFICIAL LUNG

BACKGROUND OF THE INVENTION

1. Field of the Invention

The present invention relates to artificial lungs (oxygenators). More precisely, the present invention relates to artificial lungs which are used during cardiopulmonary surgical operations, for example, to temporarily replace the function of a lung or lungs of a patient in order to supply blood of a patient, containing low oxygen, with oxygen. The blood containing low oxygen and blood containing high oxygen are called venous blood and arterial blood respectively hereinafter in the present specification and claims for simplicity.

Venous blood of the patient is supplied to the artificial lung of the present invention, the venous blood is oxygenated by means of the artificial lung to make arterial blood, and returned to the patient.

2. Prior Art

FIG. 4 shows a conventional artificial lung, comprising, from top to bottom, a venous blood reservoir 1, a heat exchanger 2 and a blood oxygenating element 3 comprising gas permeable membranes, which have been currently utilized for oxygenation of venous blood.

The venous blood reservoir 1 further comprises, a venous blood inlet 4 located at a top thereof, a venous blood line 5 which communicates with the venous blood inlet 4 and passes the venous blood downwards therethrough, and a cylindrical filter means 6 which receive and reserve the venous blood fed by the line 5 and filter out impurities, if any, while oozing the blood therethrough. The oozed venous blood drips downwards towards the heat exchanger 2. The filter means 6 is capable of storing venous blood a volume of from 500 to 3600 ml.

The heat exchanger 2 comprises an outer cylindrical wall 7, an inner cylindrical wall 9 coaxially disposed within the outer cylindrical wall 7, a bottom plate closing lower ends of the outer cylindrical wall 7 and the inner cylindrical wall 9, and at least one heat exchanger tube 8. A tubular space is defined between the outer and inner cylindrical walls 7,9, above the bottom plate. The tubular space is partitioned from the inner side of the cylindrical filter means 6 by walls of the filtering means 6. An outlet nozzle 10 is disposed at a lower part of the outer cylindrical wall 7 so that the tubular space communicates with the outer space through the nozzle 10. The tube 8 is made of a chemically stable material such as stainless steel or aluminum and accommodated within the tubular space to surround helically the inner cylindrical wall 9. One of the ends of the tube 8 is connected to a water supply means (not shown) which supplies the tube 8 with temperature controlled water. The other end of the tube 8 is connected to a waste water disposal line (not shown). Inside of the inner cylindrical wall 9 is a vacant space.

The blood oxygenating element 3 has a cylindrical body, a venous blood inlet 11 and an arterial, blood outlet 12 both inlet 11 and outlet 12 providing communication between the outer space and the inside space of the cylindrical body. There are no interconnections between the inner space of the heat exchanger 2 and the inner space of the oxygenating element 3 except through the outer space. The element 3 also has an oxygenous gas inlet which is connected to an oxygenating gas supply means (not shown) and a gas outlet. The inner space of the oxygenating element 3 is separated into at least two chambers, one of the chambers communicating with the venous blood inlet 11 and the arterial blood outlet 12, the other of the chambers communicating with the oxygeneous gas inlet and the gas outlet, both chambers contacting each other through gas permeable membranes (not shown).

Operation of the above-mentioned conventional artificial lung is explained as follows.

The venous blood is first supplied to the venous blood reservoir 1 through the venous blood inlet 4. The venous blood goes down through the venous blood line 5 and is reserved temporarily in the cylindrical filter means 6. The venous blood gradually oozes through the filter means 6 and proceeds into the heat exchanger 2. The impurities which may be contained in the venous blood is filtered from the blood by means of the filter means 6.

The venous blood supplied to the heat exchanger 2 goes down contacting with the heat exchanger tube 8, and is temporarily reserved in the tubular space of the heat exchanger 2. Meanwhile, water, of which the temperature is controlled by a water supply means, is supplied to the heat exchanger tube 8 to flow therethrough. The temperature of the venous blood is regulated to a prescribed temperature by means of heat exchange between itself and the water passing through the tube 8. The venous blood, of which the temperature is regulated as described above, then goes out of the heat exchanger 2 through the outlet nozzle 10.

The venous blood goes out of the heat exchanger 2, received and pumped out by a blood pump (not shown in FIG. 4), and goes into the blood oxygenating element 3 through the venous blood inlet 11. Meanwhile, an oxygenous gas flows into one of the chambers formed inside the cylindrical body of the element 3 through the oxygenous gas inlet and goes out of it through the gas outlet. The venous blood passes through the other chamber, oxygenated through the gas permeable membrane partitioning the chambers, transformed to arterial blood, and goes out of the element 3 through the arterial blood outlet 12.

FIG. 5 schematically shows the conventional artificial lung while in operation. A patient 50 is laid down on an operating table. An artificial lung is positioned on a floor 52. The venous blood is lead downwards to the artificial lung from the patient 50 by virtue of gravity. The venous blood passes through the artificial lung, is transformed to arterial blood and returns to the patient. The propulsion to pass the blood through the filter means 6 and the heat exchanger 2 is generated by the gravity force. The blood is then pushed out by means of the blood pump 51 to go through the oxygenating element 3 and to return to the patient 50.

The above-mentioned conventional artificial lung has following inconveniences.

As mentioned above, the propulsion to pass the venous blood through the filter means 6 and the heat exchanger 2 depends on gravity. In order to guarantee a sufficient flow of blood through them, it is necessary to install the artificial lung so that the surface 53 of the venous blood reserved in the venous blood reservoir 1 is at least 700 mm lower than the patient 50. On the other hand, the oxygenating element 3 is about 300 mm in height. The heat exchanger is about 150 mm in height. The level of the surface 53 is normally determined, considering various uncertainties, to be 100 mm higher from the bottom of the reservoir 1 generally. Therefore, the surface 53 of the venous blood becomes at least about 550 mm higher than the floor 52.

The level of the operating table 13 consequently becomes at least 1250 mm above the floor 52 (sum of 700 mm and 550 mm). The level of the table 13 is too high for the surgical staffs to operate on it. So, footstools are often positioned around the operating table 13 so that the staff may work thereon. But it is not convenient to work on the footstools, for the people are obliged to climb up and down the footstools and to pay attention not to fall down from them inadvertently. The footstools obstruct the layout of surgical equipments, also.

SUMMARY OF THE INVENTION

In the light of the above-mentioned inconveniences residing in the conventional artificial lungs, the present invention has an object of providing an artificial lung which does not require raising the operating table excessively high. The present invention meets with this requirement by lowering the height of the blood surface 53 from the floor 52. It becomes possible to lower the blood surface 53, by means of a compost oxygenating element 3 and installing it within a cylindrical space inside the inner cylindrical wall 9 of the heat exchanger 2. A compact oxygenating element 3 which can be used for this purpose is disclosed in a U.S. Patent Application Ser. No. 07/037,117 which was filed on Apr. 10, 1987 and now is subjected to examination.

More specifically, the present invention has the following construction.

An artificial lung according to the present invention comprises:

(a) a venous blood reservoir to receive and reserve venous blood;

(b) a heat exchanger comprising an outer cylindrical wall, an inner cylindrical wall, and at least one heat exchanger tube having a tube wall, said outer and inner cylindrical walls being disposed coaxially to form a tubular space therebetween, said at least one tube being disposed within said tubular space communicating with a feed water line to receive water of a predetermined temperature, and said tubular space, outside said tube, communicating with said venous blood reservoir to receive said venous blood so that a temperature of said venous blood is regulated by means of heat-exchange between said water and said venous blood through said fiber wall; and (c) a blood oxygenating means, disposed within said inner cylindrical wall, comprising a cylindrical body defining a cylindrical space and at least one gas permeable membrane separating said cylindrical space into a first space and a second space, said first space receives said venous blood from said heat exchanger and said second space is communicating with an oxygenous gas feed line so that said blood is oxygenated by capturing said oxygenous gas through said gas permeable membrane.

In a preferred embodiment, the venous blood reservoir is partially composed of a filter means so that the venous blood reserved in the reservoir is filtered and drips gradually downwards after filtering out the impurities and bubbles. The filter means may be in a cylindrical form so that venous blood is contained temporarily therein and oozes after filtration.

In a preferred embodiment, the heat exchanger tube is wound around said inner cylindrical wall helically so as to generally fill said tubular space formed between said outer cylindrical wall and said inner cylindrical wall.

The blood oxygenating means preferably comprises upper and lower partitions closing upper and lower ends of the cylindrical body respectively. The gas permeable membrane is in a form of a prescribed number of hollow fibers. The upper and lower ends of each of the hollow fibers are received leak-tightly by the upper and lower partitions respectively. This construction can be achieved according to the following procedure, for example. First, a prescribed number of hollow fibers having open opposite ends are provided. Then, both ends of the fibers are dipped into a molten resin material so that the spaces formed between the fibers and the hollow spaces within the fibers are stopped up by the resin material. Finally, both ends of the fibers are cut off together with a portion of the resin so that plate-like resins, that is partitions, remain with central portions of the fibers bonding leak-tightly to the fibers. The inner hollow space within each fiber opens outwards at both extremities through the plate-like resin. The above mentioned first space corresponds to a space formed within the cylindrical body and the second space corresponds to a space formed inside said hollow fibers communicating with a space over the upper partition and a space below the lower partition. The hollow fibers may preferably form a plurality of fiber bundles composed of a plurality of said fibers. The bundles may be wound spirally around an axis of the cylindrical body in a plurality of layers, direction of winding for layers interchanging layer by layer so that slitty (narrow) vacant spaces are formed between the hollow fibers, fiber bundles and layers.

The gas permeable membrane is preferably made of a biocompatible material selected out of silicon membrane, policarbonate membrane, polyolefin porous membrane, regenerated cellulose membrane, polysulfon membrane, porous nylon membrane, porous polyester membrane, porous acrylic membrane, or porous fluorine resin membrane.

DETAILED DESCRIPTION OF THE PREFERRED EMBODIMENTS OF THE INVENTION

Preferred embodiments of the present invention are explained hereinafter referring to the attached drawings for examples.

Figure 1:
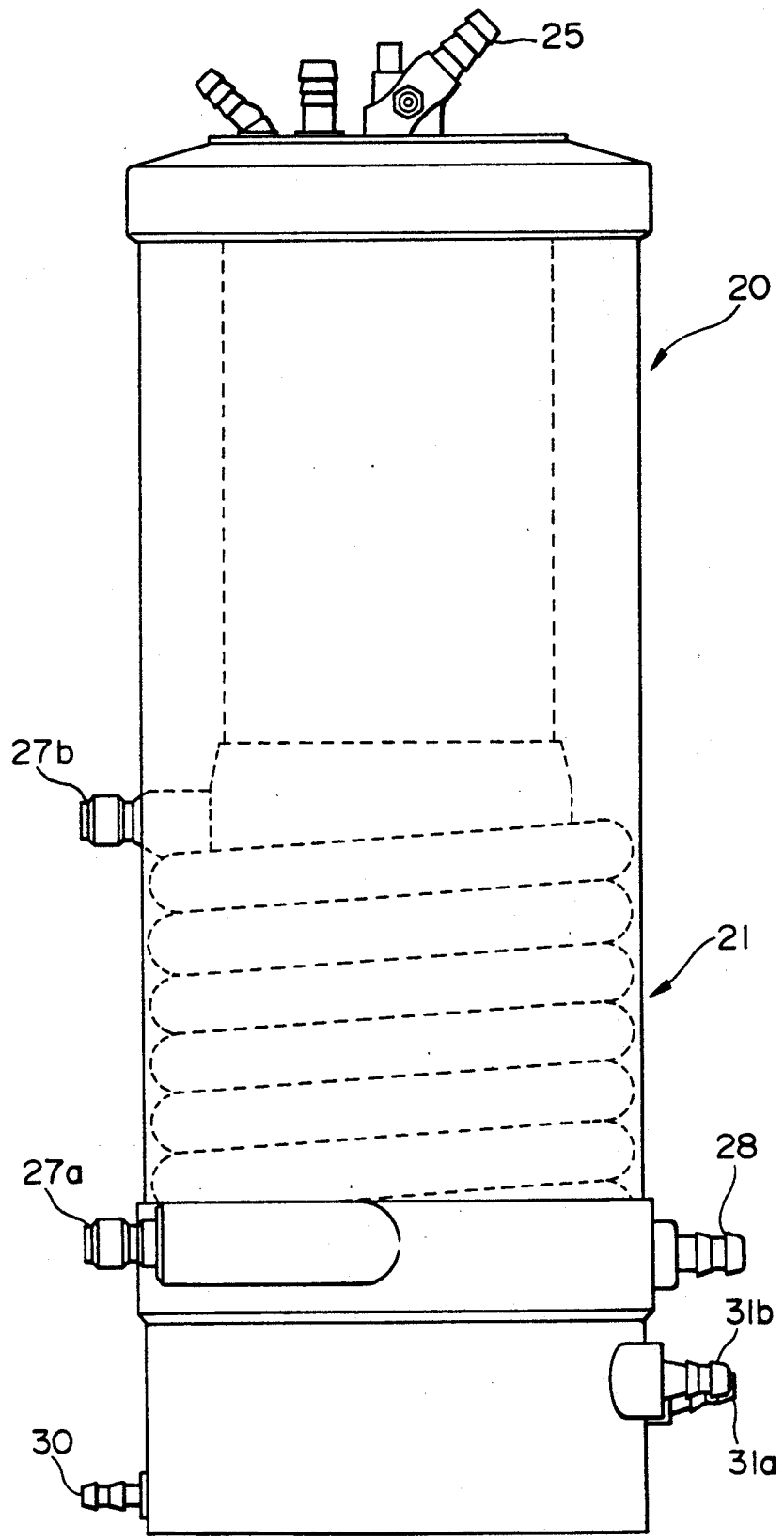
FIG. 1 is an elevational view of an artificial lung according to the present invention.
Figure 2:
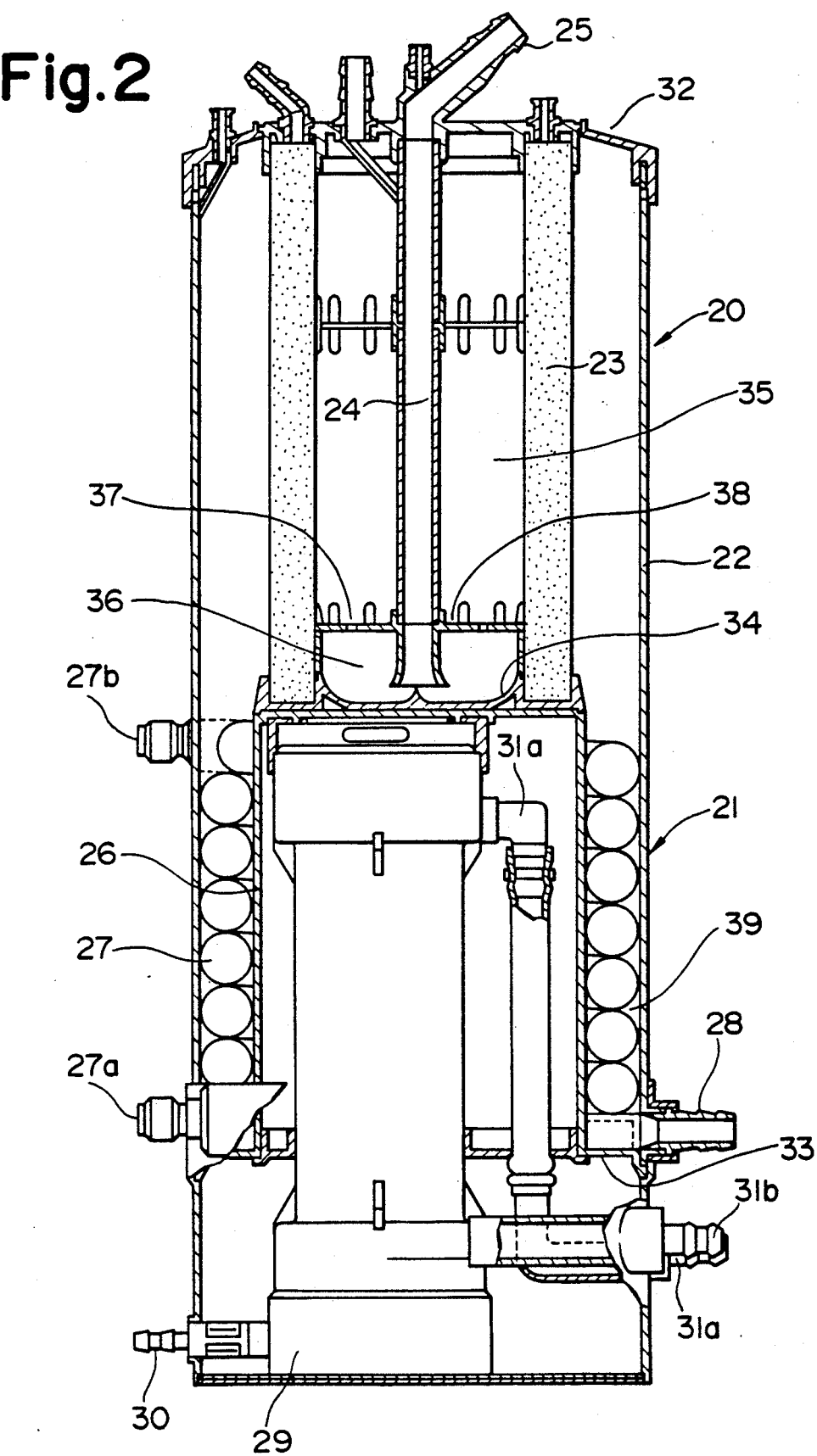
FIG. 2 is a partially cut-off view of the artificial lung of which an elevational view is shown in FIG. 1.

FIGS. 1 and 2 show a preferred embodiment of the present invention. The artificial lung according to the present embodiment comprises, at its upper part, a cylindrical jacket 20, a cylindrical filter means 23 disposed in the jacket 20 coaxially to the jacket 20, an annular covering 32 which closes an upper part of a tubular space formed between the jacket 20 and the filter means 23, a bottom plate 34 which closes a lower part of a cylindrical space defined inside the filter means 23, and a downtube 24 which is disposed coaxially to the filter means 23, opens to outer space at an upper end through an inlet nozzle 25 and opens closely above the bottom plate 34 at a lower end. A diaphragm 38 is located at a lower part of the cylindrical space inside the filter means 23 so as to separate the space into an upper space 35 and a lower space 36. Communication apertures 37 are formed through the diaphragm 38 to communicate with the upper space 35 and the lower space 36.

At a lower part of the artificial lung, there is an inner cylindrical wall 26 which is disposed coaxially to the jacket 20 to form a tubular space 39 between itself and the jacket 20, a heat exchanger tube 27 wound helically around the inner cylindrical wall 26 to generally fill the tubular space 39. The heat exchanger tube 27 is connected to a water supply means (not shown) through a water inlet nozzle 27b at its upper end and connected to a water disposal means (not shown) through a waste water outlet nozzle 27a at its lower end. Water, of which the temperature is controlled by means of the water supply means, flows through the heat exchanger tube 27. The tubular space 39 is closed at its lower end by an annular bottom plate 33 and communicates with an outer space through a venous blood outlet nozzle 28 attached at a lower part of the jacket 20.

Figure 3:
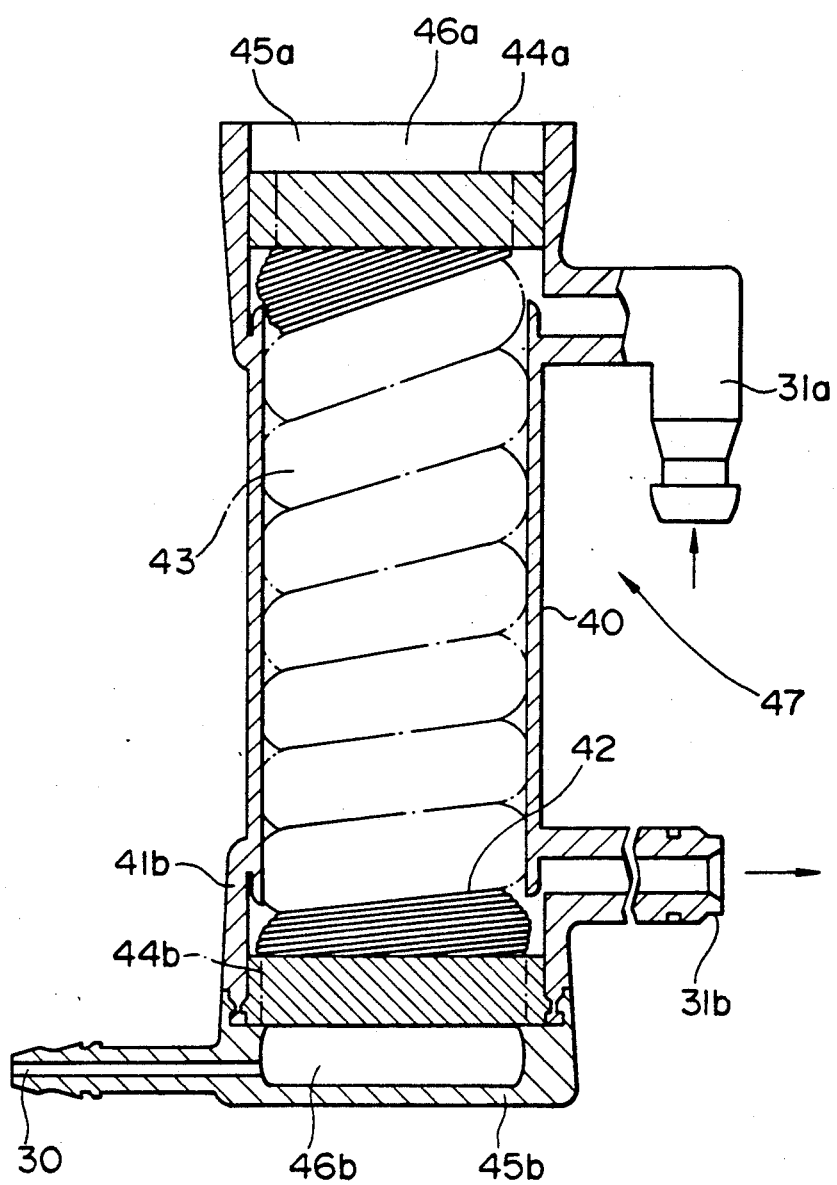
FIG. 3 is a partially cut-off view of a blood oxygenating element.
Figure 4:
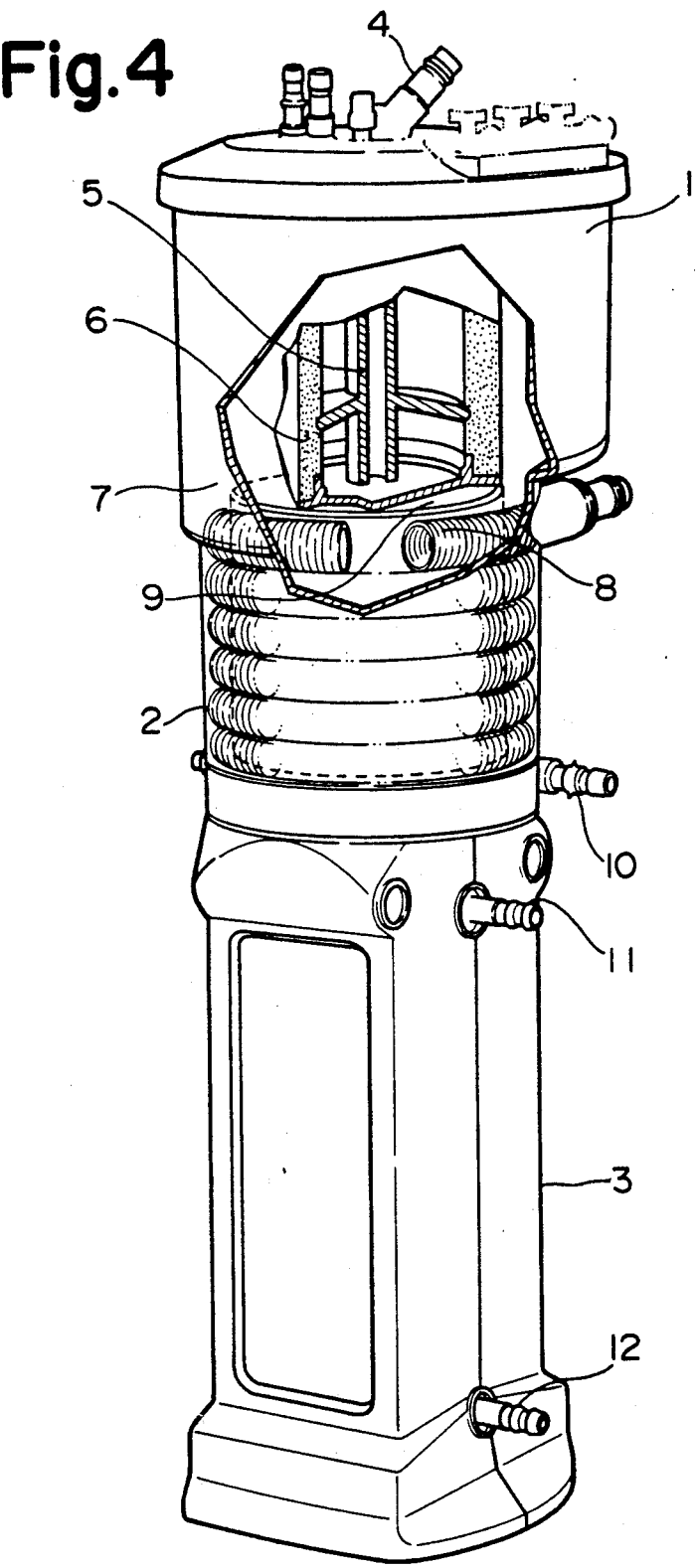
FIG. 4 is a partially cut-off perspective view of a conventional artificial lung.
Figure 5:
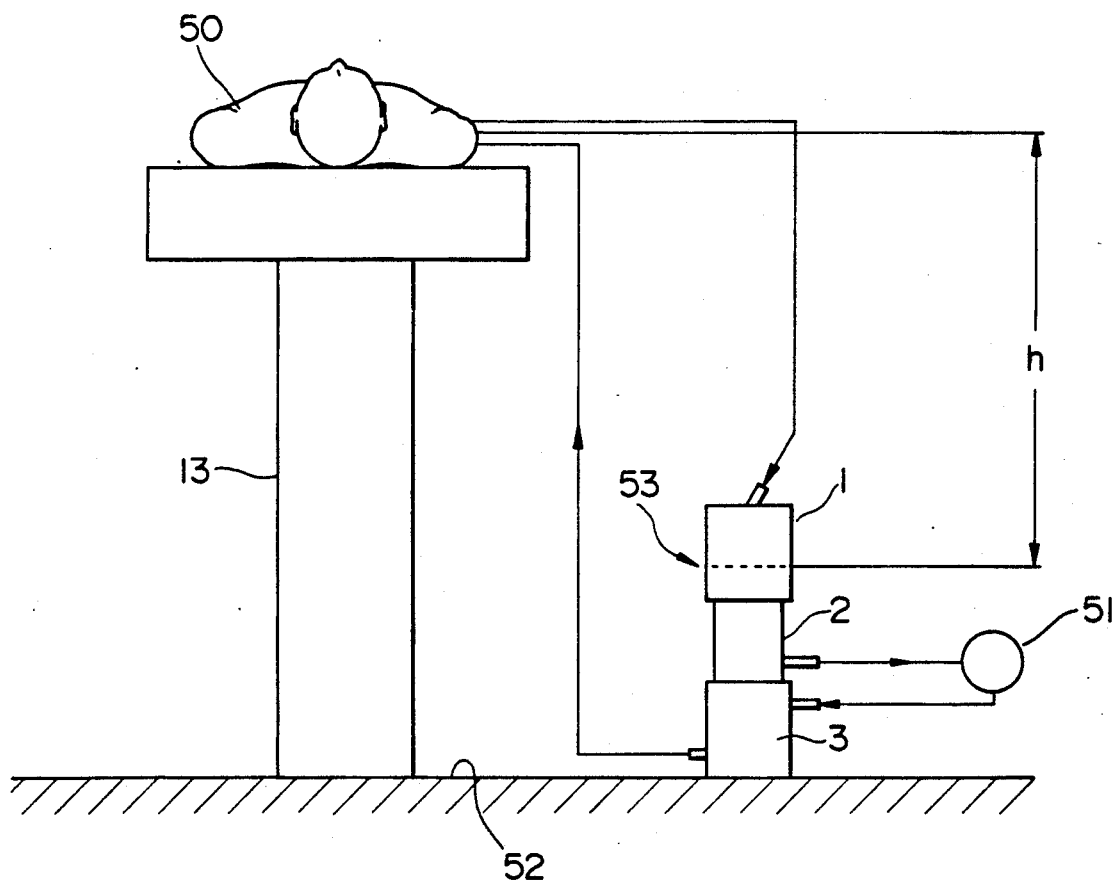
FIG. 5 is a sketch showing schematically the usage of an artificial lung during surgical operation.

Inside the inner cylindrical wall 26, there is provided an oxygenating element 47, shown in FIG. 3 in more detail, which comprises a cylindrical body 40, an upper partition member 44a, a lower partition member 44b, an upper head cover 45a, a bottom head cover 45b, and hollow fiber bundles 43 comprising hollow tubes 42. Each of the upper and lower partition members 44a, 44b holds the respective end of the fiber bundles 43 so that the space between the fiber bundles 43 are filled thereby leak-tightly and the inner space of the fiber bundles opens outwards. Therefore, the head space 46a, formed above the upper partition member 44a, communicates with the bottom chamber 46b, formed by the lower partition member 44b and the bottom head cover 45b, through the inner space of the hollow tubes 42. The bottom chamber 46b is also connected to an oxygenous gas supply unit (not shown) through a gas inlet 30 and the head space 46a communicates with a gas disposal line (not shown). The inner space defined by the cylindrical body 40 is communicating with the outer space through a venous blood inlet nozzle 31a which is to be connected to a blood pump (not shown) at an upper part, and an arterial blood outlet nozzle 31b which is to be connected to a patient (not shown) to return the oxygenated arterial blood.

The inner diameter of the hollow tubes 42 is 30 to 1000 microns. The material to be used for the hollow tubes 42 is a gas permeable and bio-compatible material such as silicon membrane, policarbonate membrane, polyolefin porous membrane, regenerated cellulose membrane, polysulfonate membrane, nylon porous membrane, polyester porous membrane, acrylic porous membrane, or fluorine resin porous membrane. The hollow fiber bundle 43 is composed of 24 hollow fibers, for example, and wound spirally around a core rod (not shown) so that the angle made by the axis and a tangential line of a hollow fiber 42 make an angle of 60 degree when they are seen from the side. Each hollow fiber 42 is hold leak-tightly by the upper partition member 44a and the lower partition member 44b at its both ends respectively.

The hollow fiber bundles 43 are wound to form a plurality of bundle layers, each layer being wound spirally so that the direction of the winding interchanges, layer by layer. Diameter of the outermost layer is generally equal to the inner diameter of the cylindrical body 40 of the oxygenating element 47. By virtue of above-mentioned spiral winding of the bundles 43, slitty (narrow) vacant spaces are formed between the bundles 43 and also between the hollow fibers 42. Also by virtue of the winding, bundle layers co-act to resist against the external pressure which may act to press the layers inwards when venous blood is pumped into the cylindrical body 40 through the venous blood inlet nozzle. Therefore, the slitty vacant spaces used to flow blood therethrough are kept constant during function.

At the outer surface of the outer most layer, ridges and grooves are formed along the spiral winding. Because the outermost diameter of the winding, that is the outer diameter of ridges, is generally equal to the inner diameter of the cylindrical body 40, the outermost hollow fibers 42 comes in contact with the cylindrical body 40 spirally along the ridges. The contact becomes more tight when oxygenous gas flows through the hollow fibers 42. Therefore, there is not a direct flow path for the venous blood pumped into the inner space of the cylindrical body 40, and the venous blood flows spirally either through the grooves formed around the outer side of the spiral winding or through the slitty vacant spaces formed between the hollow fibers.

Above-mentioned construction of the oxygenating element 47 increases the effective area for oxygenating of the venous blood. In other words, volume of the oxygenating element can be made smaller by virtue of above construction while maintaining required oxygenation capacity. Thus, it becomes possible to install the oxygenating element 47 within the cylindrical space inside the inner cylindrical wall 26 of the heat exchanger.

Oxygenation procedure of venous blood according to the artificial lung of the present embodiment is now explained as follows.

The venous blood to be oxygenated is first fed through the inlet nozzle 25, goes down through the downtube 24, and reserved in the lower chamber defined by the bottom plate 34 and the diaphragm 37. When the surface of the reserved blood reaches the diaphragm 37, the blood begins to overflow through the apertures 37 formed through the diaphragm and begins to be temporarily reserved in the cylindrical space defined by the filter means 23. Then the blood begins to ooze through the filter means 23 and drip downwards along the filter means 23. By means of this filtration process, impurities and bubbles which may be contained in the blood are filtered from the blood.

The blood dripping along the filter means 23 is reserved within the tubular space 39 formed between the jacket 20 and the inner cylindrical wall 26. The blood proceeds downwards gradually spirally along the heat exchanger tube 27, wherein temperature controlled water is flowing. Therefore, temperature of the blood is regulated to a prescribed temperature by virtue of heat exchange between the water and the blood through the tube 27 before it arrives at the bottom of the tubular space 39. The blood goes out of the tubular space 39 through the outlet nozzle 28 and flows into a blood pump (not shown). Up to this point, the blood flows only by virtue of the gravity force. The water which flows through the tube 27 may be disposed after flowing out of the water outlet nozzle 27b or may be returned to the water supply means for re-heating or re-cooling and re-circulation.

The blood, flowing out of the outlet nozzle is received by the blood pump and pumped out therefrom. The blood is supplied to the oxygenating element 47 through the venous blood inlet nozzle 31a. The blood enters into the cylindrical space defined by the cylindrical body 40 of the element 47, goes down through the slitty vacant spaces formed between adjacent hollow tubes 42. While the blood goes through the vacant spaces, it captures oxygen thereinto from the oxygenous gas, flowing through the fibers 42, and through the fiber wall which is made of a gas permeable material. Thus the venous blood entering through the venous blood inlet 31a is transformed to arterial blood as a result of this oxygen capturing. The oxygen abundant arterial blood gets out of the hollow fibers 42, is gathered in the bottom chamber 46b, and flows out of the arterial blood outlet nozzle 30 to be returned to the patient. The blood flow after the blood pump to the patient is generated by the blood pump.

By having a compact oxygenating element and installing the element in a hollow space formed within the inner wall of the heat exchanger, as mentioned above, total height of the artificial lung is lowered by 200 mm. Therefore, height of the operating table can also be lowered by 200 mm, from 1250 mm to 1050 mm. Thus, it became possible for the surgical staff to work without bothersome footstools.

Further, because of a lowered gravity center, the artificial lung according to the present invention is more stable when being kicked at or the floor trembles, thus increasing the reliability and safety.

A compact oxygenation element is used in the above embodiment. But the oxygenation element should not necessarily be limited in the above compact one. In that case, diameter of the heat exchanger may increase to accommodate the oxygenation element therein.

What is claimed is:

1. An artificial lung comprising:
   (a) a venous blood reservoir to receive and reserve venous blood;
   (b) a heat exchanger comprising an outer cylindrical wall, an inner cylindrical wall, and at least one heat exchanger tube having a tube wall, said inner and outer cylindrical walls being disposed coaxially to form a tubular space therebetween, said at least one heat exchanger tube being disposed within said tubular space communicating with a feed water line to receive water of a predetermined temperature, and said tubular space outside said at least one heat exchanger tube communicating with said venous blood reservoir to receive venous blood so that the temperature of venous blood is regulated by means of a heat-exchange through said tube wall between water and venous blood, wherein said venous blood reservoir comprises a downtube, a reserve chamber, a diaphragm having means defining at least one aperture, and a cylindrical filter, said downtube leading the venous blood into said reserve chamber, said reserve chamber being covered by said diaphragm so that the venous blood is contained therein and overflows through said at least one aperture, said cylindrical filter covering an upper area of said reserve chamber so that the overflowed venous blood is contained temporarily therein and oozes therethrough gradually; and
   (c) a blood oxygenating means, disposed within said inner cylindrical wall, comprising a cylindrical body defining a cylindrical space and at least one gas permeable membrane separating said cylindrical space into a first space and a second space, said first space being arranged to receive said venous blood from said heat exchanger and said second space communicating with an oxygen containing gas feed line so that blood is oxygenated through said at least one gas permeable membrane.

2. An artificial lung according to claim 1, wherein said removes impurities and bubbles, which may be contained in the venous blood.

3. An artificial lung according to claim 1 or 2 wherein the reserve chamber, diaphragm and filter are positioned above said heat exchanger, venous blood being enabled thereby to pass through said filter by virtue of gravity force.

4. An artificial lung according to claim 1, wherein said heat exchanger tube is wound around said inner cylindrical wall helically so as to generally fill said tubular space formed between said outer cylindrical wall and said inner cylindrical wall.

5. An artificial lung according to claim 4, wherein an outer diameter of said heat exchanger tube is generally equal to a thickness of said tubular space formed between said outer cylindrical wall and said inner cylindrical wall so that the venous blood supplied to said heat exchanger flows helically through a space formed between adjacent windings of said heat exchanger tube while heat exchanging through said tube wall.

6. An artificial lung according to claim 1, wherein said blood oxygenating means comprises upper and lower partitions closing upper and lower ends of said cylindrical body respectively, and said at least one gas permeable membrane is in the form of a prescribed number of hollow fibers, upper and lower ends of each of said hollow fibers being received in a leak-tight manner by each of said upper and lower partitions, respectively, so that said first space corresponds to a space formed within said cylindrical body and said second space corresponds to a space formed inside said hollow fibers communicating with a space over said upper partition and a space below said lower partition.

7. An artificial lung according to claim 6, wherein said hollow fibers form a plurality of fiber bundles composed of a plurality of said fibers, said bundles being wound spirally around an axis of said cylindrical body in a plurality of layers, wherein the direction of winding for adjacent layers interchanges layer by layer so that narrow open spaces are formed between said hollow fibers, and fiber bundle layers.

8. An artificial lung according to claim 7, wherein the outermost diameter of said layers is generally equal to the inner diameter of said cylindrical body, a venous blood inlet is formed at one of upper or lower ends of said cylindrical body to receive the venous blood, and an arterial blood outlet is formed at the other of said upper or lower ends of said cylindrical body for exit of arterial blood so that the venous blood flows from said venous blood inlet to said arterial blood outlet through said narrow open spaces while capturing oxygen therein.

9. An artificial lung according to claim 6, 7 or 8, wherein said at least one gas permeable membrane is made of a bio-compatible material selected from the group consisting of silicon membrane, polycarbonate membrane, porous polyolefin membrane, regenerated cellulose membrane, polysulfon membrane, porous nylon membrane, porous polyester membrane, porous acrylic membrane, and porous fluorine resin membrane.

* * * * *